United States Patent
Kinoshita et al.

(10) Patent No.: US 7,098,298 B2
(45) Date of Patent: Aug. 29, 2006

(54) METHOD FOR PRODUCING POLYHYDROXYALKANOATE CRYSTAL

(75) Inventors: Koichi Kinoshita, Kakogawa (JP); Fumio Osakada, Okayama (JP); Yasuyoshi Ueda, Himeji (JP); Karunakaran Narasimhan, West Chester, OH (US); Angella Christine Cearley, Hamilton, OH (US); Kenneth Yee, Cincinnati, OH (US); Isao Noda, Fairfield, OH (US)

(73) Assignees: Kaneka Corporation, Osaka (JP); Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/992,133

(22) Filed: Nov. 19, 2004

(65) Prior Publication Data

US 2005/0228168 A1 Oct. 13, 2005

Related U.S. Application Data

(60) Provisional application No. 60/524,622, filed on Nov. 25, 2003.

(30) Foreign Application Priority Data

Nov. 21, 2003 (JP) .............................. 2003-392467

(51) Int. Cl.
*C08F 6/00* (2006.01)
(52) U.S. Cl. ...................... 528/480; 426/623; 426/635; 528/191; 528/495; 528/499
(58) Field of Classification Search ................ 528/191, 528/480, 495, 499; 426/623, 635
See application file for complete search history.

(56) References Cited

U.S. PATENT DOCUMENTS

| | | | |
|---|---|---|---|
| 4,562,245 A | 12/1985 | Stageman | |
| 4,968,611 A | 11/1990 | Traussnig et al. | |
| 5,646,238 A | 7/1997 | Ikeda et al. | |
| 5,894,062 A | 4/1999 | Liddell | |
| 5,942,597 A | 8/1999 | Noda et al. | |
| 6,087,471 A * | 7/2000 | Kurdikar et al. | 528/480 |
| 2002/0090687 A1* | 7/2002 | Tripathi et al. | 435/135 |
| 2005/0191629 A1* | 9/2005 | Walsem et al. | 435/6 |

FOREIGN PATENT DOCUMENTS

| | | | |
|---|---|---|---|
| EP | 0707024 | * | 4/1996 |
| JP | 59-205992 | | 12/1985 |
| JP | 2-69187 | | 11/1990 |
| JP | 10-504460 | | 4/1999 |
| WO | WO 9707229 | * | 2/1997 |
| WO | WO 9945122 | * | 9/1999 |

* cited by examiner

*Primary Examiner*—Terressa Boykin
(74) *Attorney, Agent, or Firm*—Kenyon & Kenyon LLP

(57) ABSTRACT

The present invention provides a method for conveniently obtaining a biodegradable polyhydroxyalkanoate by a solvent extraction method. A method for producing a polyhydroxyalkanoate crystal comprises precipitating a polyhydroxyalkanoate crystal using a monohydric alcohol having 4 to 10 carbon atoms as a extraction solvent, keeping a polyhydroxyalkanoate solution containing 0.1 to 10% by weight of water relative to the total amount of the solution warm at 70° C. or higher, and cooling the solution to below 70° C.

10 Claims, No Drawings

METHOD FOR PRODUCING POLYHYDROXYALKANOATE CRYSTAL

This application claims priority to Japanese Patent Application No. 2003-392467 filed 21 Nov. 2003 and also claims benefit under 35 USC § 119(e) of U.S. Provisional Application No. 60/524,622 filed 25 Nov. 2003, the contents of which are incorporated herein by reference in their entireties.

TECHNICAL FIELD

The present invention relates to a method for efficiently producing a polyhydroxyalkanoate acid accumulated in a biomass using a solvent.

BACKGROUND ART

A polyhydroxyalkanoate (hereinafter referred to briefly as "PHA") is a biodegradable and thermoplastic polyester which is synthesized and accumulated as an energy storage substance in cells of a variety of microorganisms. A PHA, which is produced by microorganisms using natural organic acids or oils as carbon sources, is completely biodegraded by a microorganism in soil or water to be taken up in the carbon cycle of the natural world. Therefore, a PHA can be said to be an environment-conscious plastic material which hardly causes adverse effects for ecological system. In these years, a synthetic plastic came into a serious social problem in view of environment pollution, waste disposal and oil resource, thus a PHA has attracted attention as an eco-friendly green plastic and its practical applications are longed for.

When a PHA is produced on a commercial scale, there is a case in which microorganisms innately producing a PHA are used, or a case in which a PHA synthetic gene is recombinated into a microorganism or a plant to obtain a transformant, which is to be used as a host for production. In both cases, since a PHA is accumulated in the biomasses, the PHA is to be produced by recovering the PHA-containing biomass, and separating and purifying the PHA from the biomass.

As regarding the separation and purification of a PHA from a biomass, a method is known as the most convenient which comprises extracting a PHA using a PHA-soluble solvent, crystallizing the resultant using a poor solvent, and recovering the PHA as a crystal. For example, there is a method comprising drying a biomass in which a PHA is accumulated, extracting the PHA from the dried biomass using a halogen-containing organic solvent such as chloroform and methylene chloride, and then mixing the extract with a poor solvent such as methanol and hexane to precipitate and recover the PHA (see Japanese Kokai Publication Sho-59-205992). With these extraction solvents, a PHA can be extracted from only a dried biomass, therefore a process for drying the biomass obtained from a culture broth is required. In addition, there is such a problem that a halogen-containing organic solvent in connection with the environmental regulation is used.

Japanese Kokai Publication Hei-02-69187 describes a method for extracting a PHB (a homopolymer of 3-hydroxybutyrate) from a wet biomass using a solvent, but all the solvents used in this publication are specific ones such as propanediol and glycerol formal, and are insufficient for commercial scale application from an economical point of view, etc.

Moreover, Japanese Kohyo Publication Hei-10-504460 discloses an extraction using a solvent having preferable water-miscibility. In this publication, methanol, ethanol and isopropanol are mentioned, but with these solvents, a PHA cannot be extracted unless the biomass is treated under pressurized condition at 100° C. or higher, which is far exceeding the boiling point. There is also concern that a significant molecular weight decrease may occur in the dissolution at a high temperature of 140° C. applied in Example 1 or 2. Furthermore, there is described that a hard and opaque gel is formed by cooling, and then the gel is compressed using a rotation roll. However, the present inventors experienced that when a polymer became a hard and opaque gel, it was no longer possible to brush away the gel from a reaction container, and it became substantially impossible to recover a PHA.

In U.S. Pat. No. 5,942,597, a PHA is recovered mainly from a plant using a solvent. In this patent, the recovery is carried out at a PHA concentration of 1%, and the amount to be used of the solvent becomes huge in such low PHA concentration, thus this method is substantially difficult to be applied on a commercial scale. Moreover, the present inventors also experienced that gelation could not be prevented under the above-mentioned conditions, too.

As described above, when a PHA is extracted and recovered using a solvent, since the gelation in crystallization is severe, the solvent extraction method considered to be substantially convenient cannot be used. Alternatively, in order to prevent gelation, there is only a means to carry out dissolution and crystallization at a low PHA concentration. But in this case, since the recovery of a PHA becomes inefficient, it becomes too costly for commercial application in the actual state. As described above, the gelation of PHA is a serious problem. However, even though it has become one of the major causes for obstructing the practical application of a PHA. However, an effective solution which prevents gelation has still not been found.

Accordingly, the subject of the present invention is to provide a method for preventing a polyhydroxyalkanoate from galation, which is a state substantially incapable of being brushed away, and for obtaining its polymer in a quite easily recoverable state, when the polyhydroxyalkanoate is extracted using a solvent from a polyhydroxyalkanoate-containing biomass and the polyhydroxyalkanoate is crystallized.

SUMMARY OF THE INVENTION

The present inventors eagerly investigated on the above-mentioned subject, and as a result, they have found that a significant galation of a PHA could be minimized by dissolving a PHA obtained from a dry or wet biomass in a monohydric alcohol having 4 to 10 carbon atoms at 70° C. or higher, separating the extract from the biomass residue, and preparing the extract so as to contain water in 0.1 to 10% by weight, preferably 2 to 8% by weight to make the extract in water containing condition. Furthermore, they have also found that by lowering the temperature of the solution to below 70° C., the recovery amount increased, and a PHA became a state which could be recovered by filtration. Thereby, they completed the present invention.

That is, the present invention relates to a method for producing a polyhydroxyalkanoate crystal which comprises precipitating a polyhydroxyalkanoate crystal using a monohydric alcohol having 4 to 10 carbon atoms as a extraction solvent, keeping a polyhydroxyalkanoate solution containing 0.1 to 10% by weight of water relative to the total amount of the solution warm at 70° C. or higher, and cooling the solution to below 70° C.

DETAILED DESCRIPTION OF THE INVENTION

In the following, the preferred embodiment of the present invention is illustrated to describe the present invention in further detail. The extraction solvent used for the present invention is a monohydric alcohol having 4 to 10 carbon atoms. As such extraction solvents, there may be mentioned butanol, pentanol, hexanol, heptanol, octanol, nonanol, decanol, and isomers thereof. More preferred are relatively cheap monohydric alcohols with comparatively low boiling point which has 4 to 7 carbon atoms and is highly excellent in extraction and dissolution abilities. As such monohydric alcohols, butanol, pentanol, hexanol, heptanol, and isomers thereof are particularly preferred as the extraction solvent of the present invention. As the above butanol, isobutanol is preferred. As the above extraction solvent, one species or two or more can be used.

According to the preferred embodiment of the present invention, a PHA can be extracted either from a dry biomass or from a wet biomass. In both cases, the extract is prepared in such manner that water is contained in 0.1 to 10% by weight, and preferably 2 to 8% by weight in the extract. The present inventors have found that, for the first time, a significant gelation at the time of crystallization after the extraction can be moderated by this procedure. However, when the water content exceeding 10% by weight in the extract, the extraction solvent recovery becomes difficult.

According to the preferred embodiment of the extraction operation, a PHA is extracted from a biomass using one of the extraction solvent of the present invention. The PHA concentration is not particularly restricted, but the extraction solvent may be added so that the concentration becomes preferably 1 to 20% by weight, more preferably 2 to 15% by weight, and still more preferably 3 to 10% by weight. The temperature for extracting a PHA is preferably 70° C. or higher, more preferably 80° C. or higher, and still more preferably 90° C. or higher. However, the temperature preferably does not substantially exceed 100° C. in order to prevent decomposition of a PHA. Duration for extracting a PHA is not particularly restricted, but generally 20 to 150 minutes, and more preferably 60 to 120 minutes in view of obtaining preferable extraction efficiency and preventing the decomposition. Thereafter, the extraction solution is separated from an insoluble biomass. In this case, it is advantageous to use a heated filter, or a heated centrifugal separator such as a decanter. The separation may be carried out under a pressurized condition. However, if the temperature drops to below 70° C. during the separation, a PHA rapidly gelates, and solidifies later, in which case a PHA cannot be separated from the residues. Therefore, the solution is constantly kept warm at 70° C. or higher until the biomass residues are removed. Then, the extract is gradually cooled to below 70° C. to enable to increase the crystallization amount of a PHA.

The recovery of PHA is carried out by the methods well-known to the person skilled in the art such as a liquid filtration or centrifugation of a PHA solution. The recovered PHA can be washed with a solvent such as water, methanol, ethanol, butanol, acetone hexane and heptane or a mixture thereof. However, the solvent is not restricted to these. The drying of PHA is carried out by the methods well-known to the person skilled in the art such as, for example, air flush drying and vacuum drying.

The PHA as used in this specification is a generic term meaning any or all polymers composed of hydroxyalkanoates. The hydroxyalkanoate components are not particularly restricted, but specifically there may be mentioned 3-hydroxybutyrate(3HB), 3-hydroxyvalerate(3HV), 3-hydroxypropionate, 4-hydroxybutyrate, 4-hydroxyvalerate, 5-hydroxyvalerate, 3-hydroxyhexanoate(3HH), 3-hydroxyheptanoate, 3-hydroxyoctanoate, 3-hydroxynonanoate, 3-hydroxydecanoate, etc. The PHA of the present invention may be a homopolymer of one of these hydroxyalkanoates or a copolymer obtainable by copolymerizing two or more species of these. However, preferred is the copolymer obtainable by copolymerizing two or more species of these. As specific examples of the PHA, there may be mentioned PHB (a homopolymer of 3HB), PHBV (a binary copolymer composed of 3HB and 3HV), PHBH (a binary copolymer composed of 3HB and 3HH, see Japanese Patent Publication No. 2777757), PHBHV (a ternary copolymer composed of 3HB, 3HV and 3HH, see Japanese Patent Publication No. 2777757), etc. Particularly among them, a copolymer comprising 3HH as a monomer component is preferable since it has degradability as a biodegradable polymer and softness, and more preferred is PHBH.

In this case, the mol ratio of monomers constituting PHBH is not particularly restricted but ones containing 1 to 99 mol % are preferred and ones containing 1 to 30 mol % are more preferred in view of showing a preferable processability. Moreover, in view of preferable crystallinity in the crystallization, ones containing 20 mol % or less of 3HH composition are preferred and ones containing 15 mol % or less are more preferred. Particularly, ones containing 10 mol % or less of 3HH composition are preferred in view of a preferable operability. In the case of PHBHV, the compositional ratio of monomer units constituting of PHBHV is not particularly restricted, but for example, ones containing 1 to 95 mol % of 3HB unit, 1 to 96 mol % of 3HV unit, and 1 to 30 mol % of 3HH unit are preferred.

To be put into practical use, a PHA should have the average molecular weight determined by a gel chromatography method, in which polystyrene is set as a molecular weight standard, of 10,000 or more. It is more preferably 50,000 or more, still more preferably 100,000 or more, and particularly preferably 200,000 or more.

The biomass to be used in the present invention is not particularly restricted provided that it is a microorganism capable of accumulating a PHA in cells. For example, microorganisms belonging to the genus *Alcaligenes* such as *Alcaligenes lipolytica* and *Alcaligenes latus*, the genus *Ralstonia* such as *Ralstonia eutropha*, the genus *Pseudomonas*, the genus *Bacillus*, the genus *Azotobacter*, the genus *Nocardia*, the genus *Aeromonas*, the genus *Clostridium*, the genus *Halobacterium*, the genus *Rhodospirillum*, the genus *Zoogloea*, the genus *Candida*, the genus *Yarrowia*, the genus *Saccharomyces* and the like can accumulate a PHA in cells by controlling culture conditions.

Alternatively, a transformant obtainable by introducing a gene group involved with a PHA synthesis of these microorganisms may also be used. In that case, the host is not particularly restricted, and there may be mentioned microorganisms such as *Escherichia coli* and yeast (see WO01/88144), and further plants may be mentioned in addition to the above-mentioned microorganisms.

Among these, *Aeromonas caviae* belonging to the genus *Aeromonas* and the transformed cell obtainable by introducing a PHA synthetic group gene derived from said *Aeromonas caviae* are preferable since they have a synthesizing ability of PHBH excellent as a polymer. In particular, more preferred is *Ralstonia eutropha* obtainable by introducing a PHA synthase group gene of *Aeromonas caviae*. One example of said microorganisms is internationally deposited based on Budapest Treaty to the National Institute of Advanced Industrial Science and Technology International Patent Organism Depositary, Central 6, 1-1-1 Higashi, Tsukuba, Ibaraki, Japan under the name of *Alcaligenes eutrophus* AC32 (accession date: Aug. 7, 1997, accession number: FERM BP-6038).

A method for culturing the PHA-producing microorganisms mentioned hereinabove is not particularly restricted, but for example, the method well-known to the person skilled in the art disclosed in Japanese Kokai Publication 2001-340078 can be used.

In recovering a PHA, it is naturally preferable that the PHA content in the cultured microbial cell is higher. In the application for a commercial production, the PHA content in dried cells is preferably 50% by weight or more. Taking subsequent separation operations, purity of a separated polymer and the like into consideration, the PHA content is more preferably 60% by weight or more, and still more preferably 70% by weight or more.

After completion of the culture, the cell is obtained directly from a cultured broth in the dried state by general methods such as, for example, spray drying, or the cell is recovered by methods such as centrifugation or membrane separation. The recovered cell can be used in the extraction process as a dried cell, or as a wet cell moistened with water. Furthermore, a wet cell obtained by washing the recovered cell with a lipid solvent such as methanol and acetone, or one obtained by drying said cell can also be used as a cell for extracting a PHA.

The polyhydroxyalkanoate obtained according to the present invention may be formed into various forms, such as fibers, threads, ropes, textiles, fabrics, nonwoven fabrics, papers, films, sheets, tubes, boards, sticks, containers, bags, parts, foamed bodies, etc. Moreover, it may also be processed into a biaxial stretched film. The formed products may be suitably used for such fields as agriculture, fishery, forestry, gardening, medical, sanitary products, clothing, non-clothing, packaging, and others.

The biomass substances after being treated according to the present invention are preferably used as animal feed. Accordingly, the solvent to be used in the present invention is preferably in such an amount that is permissible as animal feed. However, it is preferable to substantially remove the solvent from the biomass substances.

By the method of the present invention, a polyhydroxyalkanoate can be obtained which has fluidity, and is capable of being brushed away while preventing gelation, thus it becomes possible to produce and provide a biodegradable polyhydroxyalkanoate at low cost on a commercial scale.

BEST MODE FOR CARRYING OUT THE INVENTION

Hereinafter, the present invention will be described in further detail by way of examples.

In each example mentioned below, poly(3-hydroxybutyrate-co-3-hydroxyhexanoate) (hereinafter referred to briefly as "PHBH") was produced as a copolyester. Surely, the present invention is not limited to these examples in its technical scope, and is not restricted to the production of PHBH.

EXAMPLE 1

PHBH was produced by culturing *R. eutropha* obtained by introducing a PHA synthase group gene derived from *Aeromonas caviae* (deposition number FERM BP-6038) according to the method described in Example 1 of Japanese Kokai Publication 2001-340078. After completion of the culture, cells were recovered by centrifugation to obtain wet cells, and further the cells were dried in vacuum at 50° C. for 15 hours to obtain dried cells. The dried cells had a PHBH content of 60%, the weight-average molecular weight of 1,300,000, and a 3-hydroxyhexanoate (hereinafter referred to briefly as "3HH") composition of 7 mol %. 211.4 g of isobutanol was added to 24.8 g of the dried cells, and an extraction was carried out at 100° C. for 1 hour. The solution was transferred into a jacket-type pressurized filter kept hot at 100° C., and a PHBH solution was recovered by filtration. The recovered solution was kept hot at 90° C., and 10 g of water was gradually added thereto while vigorously stirring the solution under keeping the temperature (the water content was 4.1% by weight). After completion of the addition, the solution was gradually cooled to room temperature with vigorous stirring, and then PHBH was precipitated. Said precipitate could be recovered easily by filtration. The recovered PHBH was washed with 50 g of isobutanol, and dried in vacuum at 45° C. The recovery amount was 14.1 g (95%), the purity was 99% or more, and the 3HH composition was 7 mol %. Although the molecular weight decreased to 1,100,000, it was sufficient molecular weight for processing.

EXAMPLE 2

PHBH was produced by culturing *R. eutropha* obtained by introducing a PHA synthase group gene derived from *Aeromonas caviae* (deposition number FERM BP-6038) according to the method described in Example 1 of Japanese Kokai Publication 2001-340078. After completion of the culture, cells were recovered by centrifugation to obtain wet cells. The wet cells had a PHBH content of 30%, the weight-average molecular weight of 1,300,000, and the 3HH composition of 7 mol %. 211.4 g of isobutanol was added to 50.0 g of the wet cells, and an extraction was carried out at 100° C. for 1 hour. The solution was transferred into a jacket-type pressurized filter kept hot at 100° C., and a PHBH solution was recovered by filtration. The recovered solution was kept hot at 90° C., and 5 g of water was gradually added thereto while vigorously stirring the solution under keeping the temperature (the water content was 1.9% by weight). After completion of the addition, the solution was gradually cooled to room temperature with vigorous stirring, and then PHBH was precipitated. Said precipitate could be recovered easily by filtration. The recovered PHBH was washed with 50 g of isobutanol, and dried in vacuum at 45° C. The recovery amount was 14.1 g (94%), the purity was 99% or more, and the 3HH composition was 7 mol %. Although the molecular weight decreased to 1,100,000, it was sufficient molecular weight for processing.

COMPARATIVE EXAMPLE 1

In Example 1, the PHA extract was gradually cooled to room temperature under vigorous stirring without addition of water (the water content was 0.04% by weight). As a result, the PHA was gelated, and became to have no fluidity, thus could not be brushed away. Water was added thereafter, but the fluidity was not improved, and still could not be brushed away.

In these Examples, the molecular weight was determined using Shimadzu's gel chromatography system (RI detection) equipped with Shodex K806L (300×8 mm, 2 columns-connected) (product of Showa Denko K.K.) with chloroform as a mobile phase. As the molecular weight standard sample, commercially available standard polystyrene was used. Moreover, the PHBH purity was determined by gas chromatography after methyl esterification of PHBH. The water content was determined using the infrared water balance FD-230 manufactured by Kett Electric Laboratory.

The invention claimed is:

1. A method for producing a polyhydroxyalkanoate crystal which comprises extracting a polyhydroxyalkanoate using a monohydric alcohol having 4 to 10 carbon atoms as an extraction solvent, keeping a polyhydroxyalkanoate solution containing 0.1 to 10% by weight of water relative to the total amount of the solution warm at 70° C. or higher, and cooling the solution to below 70° C. to precipitate a polyhydroxyalkanoate crystal.

2. The method for producing a polyhydroxyalkanoate crystal according to claim 1,
   wherein the monohydric alcohol is selected from among butanol, pentanol, hexanol, heptanol, octanol, nonanol, decanol, and isomers thereof.

3. The method for producing a polyhydroxyalkanoate crystal according to claim 1,
   wherein the polyhydroxyalkanoate concentration in the polyhydroxyalkanoate solution is 1 to 20% by weight.

4. The method for producing a polyhydroxyalkanoate crystal according to claim 1,
   wherein the polyhydroxyalkanoate is a copolymer obtained by copolymerizing at least two species of monomers selected from the group consisting of 3-hydroxybutyrate, 3-hydroxyvalerate, 3-hydroxypropionate, 4-hydroxybutyrate, 4-hydroxyvalerate, 5-hydroxyvalerate, 3-hydroxyhexanoate, 3-hydroxyheptanoate, 3-hydroxyoctanoate, 3-hydroxynonanoate and 3-hydroxydecanoate.

5. The method for producing a polyhydroxyalkanoate crystal according to claim 1,
   wherein the polyhydroxyalkanoate is a copolymer composed of 3-hydroxyhexanoate and at least one species of hydroxyalkanoates other than 3-hydroxyhexanoate.

6. The method for producing a polyhydroxyalkanoate crystal according to claim 1,
   wherein the polyhydroxyalkanoate is a copolymer composed of 3-hydroxyhexanoate and 3-hydroxybutyrate.

7. The method for producing a polyhydroxyalkanoate crystal according to claim 1,
   wherein the polyhydroxyalkanoate is produced by at least one microorganism selected from the group consisting of species belonging to the genus *Aeromonas, Alcaligenes, Azotobacter, Bacillus, Clostridium, Halobacterium, Nocardia, Rhodospirillum, Pseudomonas, Ralstonia, Zoogloea, Candida, Yarrowia,* and *Saccharomyces*.

8. The method for producing a polyhydroxyalkanoate crystal according to claim 1,
   wherein the polyhydroxyalkanoate is produced by a transformant obtained by introducing a polyhydroxyalkanoate synthetic gene group derived from *Aeromonas caviae*.

9. The method for producing a polyhydroxyalkanoate crystal according to claim 8,
   wherein the transformant obtained by introducing a polyhydroxyalkanoate synthetic gene group derived from *Aeromonas caviae* is *Ralstonia eutropha* obtained by introducing a polyhydroxyalkanoate synthetic gene group derived from *Aeromonas caviae*.

10. The method for producing a polyhydroxyalkanoate crystal according to claim 1,
    which comprises extracting a polyhydroxyalkanoate, and using the remaining biomass substance after decreasing its solvent content as animal feed.

* * * * *